United States Patent [19]

Gross et al.

[11] 4,239,113

[45] Dec. 16, 1980

[54] COMPOSITION FOR THE PREPARATION OF BONE CEMENT

[75] Inventors: Albert Gross; Werner Ege, both of Frankfurt am Main, Fed. Rep. of Germany

[73] Assignee: Kulzer & Co. GmbH, Bad Homburg, Fed. Rep. of Germany

[21] Appl. No.: 911,425

[22] Filed: Jun. 1, 1978

[30] Foreign Application Priority Data

Jun. 2, 1977 [DE] Fed. Rep. of Germany ....... 2724814

[51] Int. Cl.$^3$ ............................................. B65D 69/00
[52] U.S. Cl. .................................. 206/568; 260/42.18; 260/42.52; 424/81; 424/82
[58] Field of Search ........................... 260/42.18, 42.52; 206/568

[56] References Cited

U.S. PATENT DOCUMENTS 3,922,155  11/1975  Broemer et al. ............... 106/39.6 X
3,981,736   9/1976  Broemer et al. ..................... 106/39.6
4,001,939   1/1977  Gross ............................. 260/42.52 X
4,017,454   4/1977  Müller ............................. 260/42.52

FOREIGN PATENT DOCUMENTS 2501683  7/1976  Fed. Rep. of Germany .

Primary Examiner—Melvyn I. Marquis
Attorney, Agent, or Firm—Frishauf, Holtz, Goodman & Woodward

[57] ABSTRACT

A bone cement in pliable and moldable form which when applied to bone and cured has superior characteristics containing an admixture of methylmethacrylate copolymers, methylmethacrylate, and between 15 and 75% by weight of an inorganic composition of between about 90 and 99% of a bio-active glass ceramic powder having a particle size of 10–200 micrometer and between 1 and 10% of vitreous mineral fibers having a length of less than 20 mm. The composition also contains a curing catalyst and, preferably, an accelerator.

13 Claims, No Drawings

COMPOSITION FOR THE PREPARATION OF BONE CEMENT

BACKGROUND OF THE INVENTION

The present invention provides a composition for the preparation of bone cement.

Bone cements are used for, among other things, securing implants, anchoring artificial members of joints, in restoration surgery of the skull, and for joining vertebrae (discs). Plastic pastes which when cured form bone cements are produced by blending polymerized materials consisting of homopolymers or copolymers of methylmethacrylate together with suitable liquid monomers, primarily methylmethacrylate, and a catalyst system. The plastic pastes may also include additives which, when the bone cement is cured provide contrast when the portion of the body including the bone cement is x-rayed, e.g., zirconium dioxide. They may also include such adjuvants as dyes which permit observation of the cemented portion in the body. This plastic mass is inserted in the body, usually to join natural or artificial bony portions and is cured (hardened) by polymerization of the monomer. Redox catalyst systems are used which comprise an organic peroxy compound, usually dibenzoylperoxide as the catalyst, with a reducing agent (accelerator), e.g., dimethyl-p-toluidine, of which the correct chemical nomenclature is N.N-dimethyl-p-toluidine.

German patent publication No. AS-2,229,702 according to British Pat. No. 1,431,211 discloses a bone cement composition consisting of polymethylmethacrylate and a monomer mixture of methylmethacrylate and esters of methacrylic acid with higher alcohols, and a catalytic system consisting of dibenzoylperoxide and dimethyl-p-toluidine.

German disclosure document No. OS-2,501,683 discloses a composite material and its use as a bio-active bone cement. This composite material is a synthetic matrix based upon methacrylate containing a bioactive substance which stimulates the growth of the bone, and which may be a glass ceramic having an apatite crystalline phase consisting of 20-60% by weight $SiO_2$, 5-40% of $P_2O_5$, 2.7-20% of $Na_2O$, 0.4-20% $K_2O$, 2.9-30% of $M_gO$, and 5-40% of CaO. The said glass ceramic is disclosed in U.S. Pat. Nos. 3,981,736 and 3,922,155.

A fibrous material, for example, glass fibers, can be added to the composite material disclosed in German disclosure document No. OS-2,501,683 to improve its mechanical characteristics. When using such a composite material as a bone cement, for example, the hardner is added to the liquid methylmethacrylate, and then the finely powdered bio-active glass ceramic is added. When a pliable and malleable mass has been formed as a result of polymerization, the outer surface of the mass may be enriched with additional powdered glass ceramic, and then the mass may be inserted into the body and cured. In contrast with those bone cements which are produced from mixtures of polymers and monomers, the time needed for the polymerization to form the pliable mass in case of the bone cement containing the glass ceramic as disclosed in German disclosure document No. OS-2,501,683, which does not contain any polymers, is unduly long, precluding its use in surgical practice. The known bone cements containing a mixture of polymers and monomers have the advantage that the time required, after mixing thereof, for the development of a mass having a viscosity sufficiently high that it is suitable for application to the bone is considerably shorter.

The known bone cements containing the glass ceramic material contain a higher content of monomers than the conventional bone cements containing mixtures of polymers and monomers. This is a disadvantage because of the greater danger that monomer constituents of the bone cement may be carried into the blood stream.

It is an object of the present invention to provide a composition containing a mixture of copolymers of methylmethacrylate and methylacrylate useful when cured after mixing with the liquid monomers as a bone cement having advantageous processing characteristics, good mechanical properties when cured, and characteristics favorable to the development of bone structure.

THE INVENTION

The invention provides a composition containing a mixture of copolymers of methylmethacrylate and methylacrylate and about 15 to 75% by weight of an inorganic material comprising about 90 to 99% by weight of a bio-active glass ceramic in powder form and about 1 to 10% by weight of vitreous mineral fibers having a length of below about 20 mm. The particles of the bio-active glass ceramic are between 10 and 200 micrometer, and preferably between about 90 and 125 micrometer. When mixed in form for curing, the composition also contains methylmethacrylate monomer and preferably a catalyst and accelerator.

Particularly useful compositions of the present invention have a fiber content of between about 5 and 10%, preferably in conjunction with a fiber length of between about 1 and 10 mm, with fiber content of a length between about 2 and 5 mm being particularly preferred. The vitreous mineral fibers may be glass fibers, preferably bio-active glass ceramic composition. The bio-active glass ceramic compositions used in the particles and preferably the fibers, preferably may be the composition disclosed in said U.S. Pat. Nos. 3,981,736 and 3,922,155.

The invention is further illustrated in the examples wherein all parts are by weight unless expressly stated otherwise.

EXAMPLE 1

Ten parts of powder mixture consisting of 70 parts of a powdered glass ceramic having a particle size of 90-125 micrometer, 26.76 parts of the mixture of copolymerization products of methylmethacrylate with methyl acrylate, 3 parts zirconium dioxide, and 0.24 parts dibenzoylperoxide; are mixed with 3 parts of liquid comprising 98 parts of methylmethacrylate and 2 parts of di-methyl-p-toluidine. The mixture becomes pliable and formable after one minute and is then compacted under a pressure of three bar in a three-piece mold to form non-porous pieces. The polymerization (for curing) is completed at the end of 10 minutes. This is a comparative example and not an example of the compositions of the invention.

EXAMPLE 2

This is an example of the composition of the invention. Ten parts of a powder consisting of 65 parts of a glass ceramic having a particle size of 90-125 micrometer, 5 parts of glass fibers having a fiber length of 3 mm, 26.76 parts of the same copolymer mixture of methylmethacrylate and methyl-acrylate as in EXAMPLE 1, 3 parts of zirconium dioxide and 0.24 parts of dibenzoylperoxide; are mixed with 3 parts of a liquid containing 98 parts of methylmethacrylate and 2 parts of dimethyl-p-toluidine. Specimen parts are formed and cured following the procedure of Example 1

EXAMPLE 3

This example illustrates a composition of the invention. Ten parts of a powder consisting of 60 parts of glass ceramic having a particle size of 90-125 micrometer, 10 parts of glass fibers having a length of 3 mm, 26.76 parts of the mixture of the copolymer product of methylmethacrylate and methyl acrylate used in Example 1, 3 parts zirconium dioxide, 0.24 parts dibenzoylperoxide; are mixed with 3 parts of a liquid comprising 98 parts methylmethacrylate and 2 parts dimethyl-p-toluidine. Specimens are formed and cured following the procedure described in Example 1

EXAMPLE 4

This is a comparative example. Ten parts of a powder consisting of 96.76 parts of a mixture of the copolymer of methylmethacrylate and methylacrylate used in Example 1, 3 parts of zirconium dioxide, and 0.24 parts of dibenzoylperoxide; are mixed with 5 parts of a liquid containing 98 parts methylmethacrylate and 2 parts dimethyl-p-toluidine. Specimens were formed and cured following the procedure of Example 1

EXAMPLE 5

This a comparative example. Ten parts of a powder consisting of 91.76 parts of the copolymer mixture of methylmethacrylate and methylacrylate used in Example 1, 5 parts of glass fibers having a fiber length of 3 mm, 3 parts zirconium dioxide, and 0.24 parts of dibenzoylperoxide; are mixed with 5 parts of a liquid comprising 98 parts methylmethacrylate and 2 parts dimethyl-p-toluidine. Specimens were formed and cured following the procedure of Example 1

EXAMPLE 6

This is an example of the composition of the invention. Ten parts of a powder consisting of 65 parts of a glass ceramic having a particle size of 90-125 micrometer, 5 parts of glass fibers having a fiber length of 3 mm, 26.76 parts of the same copolymer mixture of methylmethacrylate and methyl acrylate as in Example 1, 3 parts of zirconium dioxide, 0.24 part of dibenzoylperoxide, and 2.12 parts of Gentamicine sulfate; are mixed with 3 parts of a liquid containing 98 parts of methylmethacrylate and 2 parts of dimethyl-p-toluidine. Specimens are formed and cured following the procedure of Example 1

EXAMPLE 7

This is an example of the composition of the invention. Ten parts of a powder consisting of 60 parts of glass ceramic having a particle size of 90-125 micrometer, 10 parts of glass fibers having a length of 3 mm, 26.76 parts of the mixture of the copolymer product of methylmethacrylate and methyl acrylate used in Example 1, 3 parts of zirconium dioxide, 0.24 part of dibenzoylperoxide, and 2.12 parts of Gentamicine sulfate; are mixed with 3 parts of a liquid comprising 98 parts methylmethacrylate and two parts dimethyl-p-toluidine. Specimens are formed and cured following the procedure described in Example 1.

EXAMPLE 8

This is a comparative example. Ten parts of a powder consisting of 96.76 parts of a mixture of a copolymer of methylmethacrylate and methylacrylate used in Example 1, 3 parts zirconium dioxide, 0.24 parts dibenzoylperoxide, and 2.12 parts of Gentamicine sulfate, are mixed with 5 parts of a liquid containing 98 parts methylmethacrylate and 2 parts dimethyl-p-toluidine. Specimens were formed and cured following the procedure of Example 1

The test specimens produced as described in each of the Examples were tested for impact strength, compression strength, and modulus of elasticity, using the standard testing methods. The values for each of the eight examples are set forth in the following table from which it is apparent that the products of the present invention, Examples 2, 3, 6 and 7 have superior properties in connection with modulus of elasticity. Examples 2, 3 and 7 have superior properties in connection with impact strength. It is further noted that the specimens of the examples prepared by mixing the admixture containing the copolymers and the peroxide with the second composition containing the monomeric methylmethacrylate and dimethyl-p-toluidine and subsequently curing, are characterized by improved mechanical properties when compared with the specimens made from polymer/monomer mixtures or polymer/monomer mixtures which also contain bio-active glass ceramic or vitreous mineral fibers. It is unexpected that the use of the preprocessed composition in the form of the combination of the copolymers in powder form, the bio-active glass ceramic powder and the vitreous mineral fiber, should result in a bone cement with improved mechanical characteristics.

TABLE

| TEST SPECIMEN | IMPACT STRENGTH [KJ/m$^2$] | BENDING STRENGTH [N/mm$^2$] | COMPRESSION STRENGTH [M Pa] | MODULUS OF ELASTICITY [N/mm$^2$] |
| --- | --- | --- | --- | --- |
| AS PER EXAMPLE 1 | 0.78 | 38.3 | 76 | 45.10$^2$ |
| AS PER EXAMPLE 2 (ACCORDING TO THE INVENTION) | 7.50 | 59.8 | 87 | 52.10$^2$ |
| AS PER EXAMPLE 3 (ACCORDING TO THE INVENTION) | 11.6 | 70.0 | 96 | 67.10$^2$ |
| AS PER EXAMPLE 4 | 4-5 | 60-80 | 82-85 | 20.10$^2$ |
| AS PER EXAMPLE 5 | 6.0 | 71.0 | — | — |
| AS PER EXAMPLE 6 (ACCORDING TO THE INVENTION) | 4.36 | 58.1 | 82 | 50.10$^2$ |
| AS PER EXAMPLE 7 (ACCORDING TO | 8.58 | 70.2 | 87 | 65.10$^2$ |

TABLE-continued

| TEST SPECIMEN | IMPACT STRENGTH [KJ/m$^2$] | BENDING STRENGTH [N/mm$^2$] | COMPRESSION STRENGTH [M Pa] | MODULUS OF ELASTICITY [N/mm$^2$] |
|---|---|---|---|---|
| THE INVENTION) AS PER EXAMPLE 8 | 1.32 | 46.8 | — | — |

Antibiotics can be added to the compositions in accordance with the present invention, as illustrated in Examples 6 and 7. Of the many antibiotics which are suitable, the following are noted for illustrative purposes:

Aminoglycoside-Antibiotics, such as Amikacin, Butirosine, Didesoxykanamicyn B (DKB), Fortimycin, Gentamycin, Kanamycin, Lividomycin, Neomycin, Netilmicin, Ribostamycin, Sagamycine, Seldomycine and it Epimeres, Sisomicin, Sorbistin, Tobramycin; Chloramphenical and its derivatives, such as Thiamiphenicol; Erythromycine; Lactone-Antibiotics, such as Novobiocin; Leucomycines, such as Josamycin, Maridomycin, Midecamycin, Spiramycin; Lincomycines, such as Clindamycin, Lindcomycin; Makrolide, such as Rosamicin; Penicillins, such as Amoxicillin, Ampicillin, Azlocillin-Natrium, Dicloxacillin-Natrium, Furoxacillin, Mecillinam, Peiperacillin; Peptid-Antibiotics such as Bacitracin, Colistimethat-Natrium, Gramicidin, Polymyxine; Rifamycine, such as Rifampicin, Rifamycin; Steroidantibiotics, such as Fusidin-acid; Streptomycine; Tetracycline, such as Doxycyclin, Minocyclin, Tetracycline; Cephalosporine, such as Cefalotin, Cefamandol, Cefazedon, Cefazolin, Cefoxitin, Cefuroxim; as well as such other antibiotics, for example, Cycloserin, Fosfomycin, and Vancomycin. The Aminoglycosid-Antiobiotics, particularly Gentamycin and its salts, are especially suitable due to their broad spectrum antibacterial action and their temperature stability. The incorporation of antibiotics in bone cements is known, e.g., from German disclosure document OS 2 022 117 according to British Pat. No. 1 349 259.

The bio-active glass ceramic used in the examples fall within the scope of those disclosed in U.S. Pats. 3,981,736 and 3,922,155 and the German disclosure document OS 2,501,683 referred to hereinbefore. The bio-active glass ceramic preferably contains between about 30 l and 60% SiO$_2$, 5 and 20% P$_2$O$_5$, 3 and 10% Na$_2$O, 3 and 10% K$_2$0, 5 and 20% MgO, and 10 and 30% CaO. The preferred glass ceramic used in the examples contains about 46.2% SiO$_2$, about 11.7% P$_2$O$_5$, about 4.8% Na$_2$O, about 0.4% K$_2$O, about 2.9% MgO, and about 34.0% CaO. The bio-active glass ceramic is used in the preferred glass powders and also the glass fibers.

The copolymer components of the compositions are formed by reacting between about 65 and 80% by weight (and preferably between 71 and 74%) of methylmethacrylate, and between 20 and 35% (and preferably between 26 and 29%) of methylacrylate. It is preferred that the copolymer contain about 73% of the methylmethacrylate and about 27% of the methyl acrylate, which composition was used in the Examples.

When used in surgery for the preparation of a bone cement, a composition of the present invention, for example, the composition of Example 2 or of Example 3, would be used by first admixing the powdered components and preferably including about 3% ZrO$_2$ as an X-ray contrast agent. This would be admixed with the liquid component containing the monomeric methyl methacrylate and a pliable mass formed. It would then be applied to the real or artificial bones being cemented, possibly, with the surface portions enriched with powdered bio-active glass particles.

Various changes and modifications of the present invention may be made within the inventive concept.

We claim:

1. An uncured bone cement composition which when cured forms a bone cement comprising between about
   (i) 15% and 75% by weight of a mixture of inorganic materials consisting essentially of between about 90 and 99% by weight of a powdered bio-active glass ceramic of a particle size between about 10 and 200 micrometer,
   said bio-active glass ceramic consists essentially of between about 20 and about 60% by weight of SiO$_2$, between about 5 and 40% P$_2$O$_5$, between about 2.7 and 20% Na$_2$O, between about 0.4 and 20% K$_2$O, between about 2.9 and 30% MgO, and between about 5 and 40% CaO,
   and between about 5 and 10% by weight of vitreous mineral fibers between about 2 and 5 mm long, admixed with
   (ii) a mixture of copolymers of methylmethacrylate and methyl acrylate.

2. The composition of claim 1 wherein said bio-active glass ceramic particles are of a size from about 90 and 125 micrometer.

3. The composition of claim 1 wherein said vitreous mineral fibers are composed of glass.

4. The composition of claim 1 wherein said vitreous mineral fibers are composed of bio-active glass ceramic.

5. The composition of claim 4 wherein said bio-active glass ceramic fibers consists essentially of between about 20 and about 60% by weight of SiO$_2$, between about 5 and 40% P$_2$O$_5$, between about 2.7 and 20% Na$_2$O, between about 0.4 and 20% K$_2$O, between about 2.9 and 30% MgO, and between about 5 and 40% CaO.

6. The composition according to each of claims 1, 2, 3, 4 or 5 which also contains monomer methyl methacrylate and a catalyst.

7. The composition of claim 1 which also contains monomeric methyl methacrylate and a peroxy compound as a catalyst.

8. The composition of claim 1 which also contains a X-ray contrast means.

9. The composition of claim 8 wherein said contrast means is zirconium dioxide.

10. The composition of claim 1 which also contains a small but effective amount of an antibiotic.

11. The composition of claim 10 wherein said antibiotic is Gentamycin or one of its pharmaceutically acceptable salts.

12. The composition of claim 1 which also contains a catalyst.

13. A two-package kit for making a bone cement comprising a first package containing the composition of claim 12 and a second package comprising a liquid containing monomeric methylmethacrylate and an accelerator.

* * * * *